United States Patent [19]

Stemmler

[11] Patent Number: 4,560,379
[45] Date of Patent: Dec. 24, 1985

[54] ABSORBENT HYGIENIC ARTICLE AND METHOD OF MANUFACTURE

[75] Inventor: Kurt Stemmler, Neuwied, Fed. Rep. of Germany

[73] Assignee: Winkler & Dunnebier Maschenfabrik und Eigengiesserei GmbH & Co. KG, Neuwied, Fed. Rep. of Germany

[21] Appl. No.: 674,683

[22] Filed: Nov. 26, 1984

[30] Foreign Application Priority Data

Dec. 6, 1983 [DE] Fed. Rep. of Germany ....... 3344032

[51] Int. Cl.$^4$ .............................................. A61F 13/16
[52] U.S. Cl. ................................. 604/368; 604/385 R; 264/112
[58] Field of Search ............... 604/365, 367, 368, 374, 604/385; 264/112

[56] References Cited

U.S. PATENT DOCUMENTS

| 2,024,976 | 12/1935 | Mathey et al. | 604/374 |
| 2,929,379 | 3/1960 | Paulsen | 604/385 R |
| 3,294,090 | 12/1966 | Younger | 604/385 R |
| 3,654,929 | 4/1972 | Nilsson et al. | 604/368 |

Primary Examiner—John D. Yasko
Attorney, Agent, or Firm—Collard, Roe & Galgano

[57] ABSTRACT

There is provided an absorbent hygienic article of generally "e" shaped cross-section with inserted superabsorbent layers, the article being stepped in a frustum shape at its front and rear ends. There is also provided a method for manufacturing the article, the blank for the article being devised individually on a flock wheel and comprised of a central member, a long side member and a short side member both disposed symmetrically about the central member. The blank is then subject to two folding steps to produce it, superabsorbent layers being applied before each of the two folding steps.

3 Claims, 8 Drawing Figures

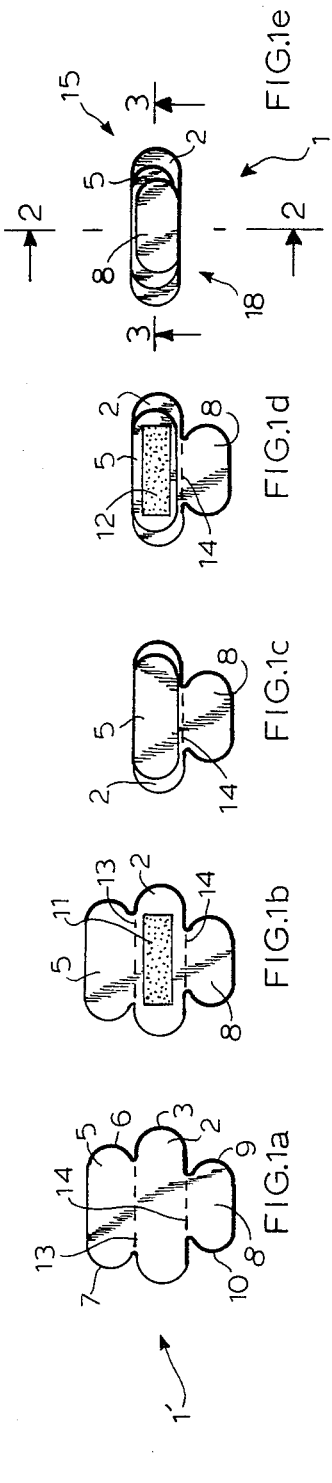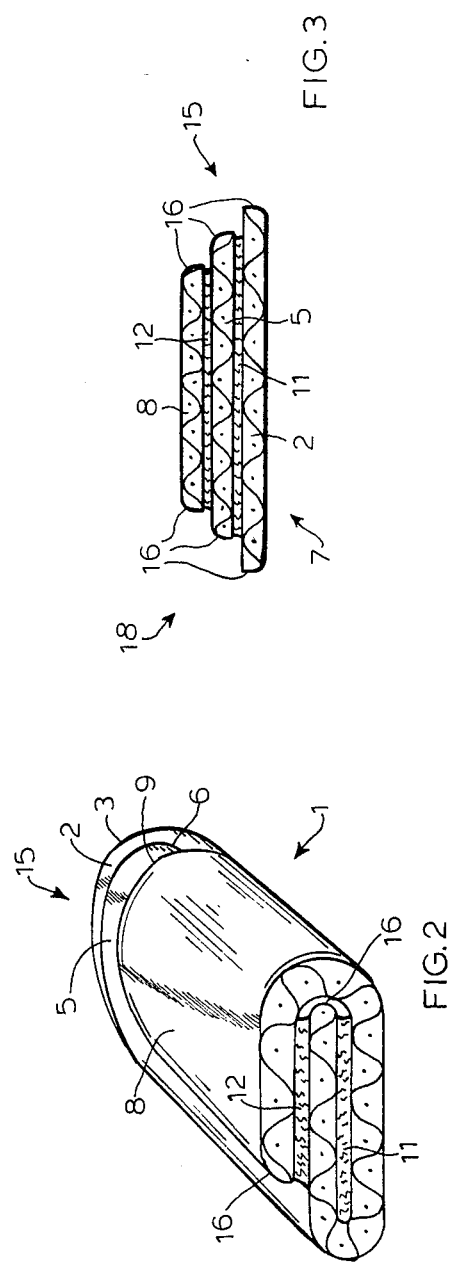

ABSORBENT HYGIENIC ARTICLE AND METHOD OF MANUFACTURE

The present invention relates to an absorbent article for hygienic purposes, such as sanitary napkins, disposable diapers or the like, having a highly absorbent body-fitting multipiece flock member, and to a method for its manufacture.

Articles of this kind are used, for example, in sanitary napkins, panty shields, disposable diapers and the like. The articles are mostly produced from hydrophilic cellulose flocks. To increase absorption and liquid retention a scattered layer or a strip of superabsorbent expanding agents is provided as an intermediate layer in the absorbent article.

One difficulty in the production of absorbent articles for hygienic purposes is to ensure that the article, while having satisfactory liquid absorptivity, is not too bulky and unwieldy. Another difficulty is to ensure that the article is shaped to fit the body for the sake of comfort. To overcome the first difficulty it has been suggested that the absorption and liquid-retention ability be enhanced by the introduction of superabsorbent expanding agents. This proposal has been carried into effect in a process for the production of absorbent articles produced from flock material in web form. Superabsorbent expanding agents are applied continuously or at intervals to one half of the web and the untreated half thereof is folded back on the treated half, a kind of endless flock sandwich arising which is parted off into discrete articles in a subsequent working step. The articles produced by this standard process are uncomfortable to wear since they do not match the shape of the body and, because of the mechanical parting-off cut, they have bulky compactings at their edges. Also, this process cannot readily be used to provide a uniformly thick flock strip of equal density, since the suction of the vacuum mesh belt in the flock layer is insufficient to produce the required compacting and felting and to always bind a uniform quantity of flocks in the flock web.

In another known process a three-member article is prepared from a relatively thin but wide flock web by cutting to shape. In this flock article an elongated central member having rounded ends merges by way of its two long sides into side members of the same geometrical shape and size as the central member. After cutting to shape these articles are given a two-stage folding in which the side members are so folded over consecutively as to lead to an absorbent article which has a generally "e" shaped cross-section. This process produces a soft thin flock web of uniform density. Also, the "e" shaped folding with the two contiguous contact surface pairs makes it possible to introduce superabsorbent materials at two places. This article is better adapted to the human anatomy in the perineal region than the articles previously described. However, the cutting, with its long line of cut, leads to unpleasant bulky compacting at the edges. Because of the "e" shaped folding these compacted edge parts are to some extent disposed one above another. Consequently, the front end and rear end of the article become so bulky as to considerably impair the wearability of the article. Also, for use in sanitary napkins and disposable diapers, it is not only unnecessary, but possibly even disadvantageous, for the "e" shaped article to be of uniform thickness over its whole length. Since this article is inherently more rigid and has useless accumulations of material at its ends, it is poorly adapted to the shape of the human anatomy. Also, the cutting of the web calls for continuous removal of the cutting waste, the same usually being returned to the flock mill by expensive extractor facilities. The cutting step also leads to the evolution of substantial quantities of cellulose dust which soil the machine and are unpleasant for the operators thereof.

It is an object of the present invention to provide an absorbent article for hygienic purposes which has adequate liquid absorption capacity, is not too bulky or unwieldy and adapts readily to the perineal region of the human anatomy, and also to provide a method for manufacturing such articles.

This object is accomplished in accordance with the present invention by an absorbent article for hygienic purposes having a highly absorbent body-fitting multi-piece flock member, wherein the absorbent member formed on a flock wheel includes an elongated cental member having rounded front and rear ends, the central member merging by way of its long sides into two symmetrically disposed side members differing in length from one another and also rounded at their front and rear ends, the long side member being folded onto the surface of the central member and the short side member being folded onto the back side of the folded long side member so that a folded absorbent article of generally "e" shaped cross-section results which is stepped frustum-fashion at its front and rear ends, and a scattered layer or strip of superabsorbent material and/or flowspreader is inserted between at least one pair of the contiguous contact surfaces of the folded together members of the article. According to the method of manufacturing the article, a flow of flock is delivered from a flock mill mainly comprising reduced cellulose by air onto the generated cylindrical surfade of a rotating flock wheel, along a predetermined vacuum path the flock is disposed into three part shaping recesses, consecutively arranged in the direction of rotation on the flock wheel, the flocks being compacted and felted to form the article blanks, the flock material projecting from the recesses is removed and returned to the flock flow, at the end of the vacuum path the three member article blanks are removed and delivered to a conveyor, on the conveyor superabsorbent material is applied to the elongated central member, and the blanks are then folded by the first long side member being folded onto the surface of the central member, then the short side member is folded onto the back side of the long side member, and superabsorbent materials being applied between the two folding steps to the back of the long side member.

The main advantage provided by the present invention is the provision of a process enabling blanks of three-member absorbent articles to be formed continuously by means of a rotating flock wheel, then the blanks are so folded individually that small "e" shaped cross-section absorbent articles result. Also, such an article has the advantage that in it there are two voids which are adapted to receive superabsorbent materials and/or flow spreaders in order to improve absorbability and liquid retention. Also, the blank formed on the flock wheel has completely soft edge zones since there are no bulky edge compactings which result because of cutting to shape. Also, due to the difference between the length of the side members and, after the folding to an "e" shape, the resulting article is stepped frustum-fashion at its ends, adapts readily to the anatomy of the perineal zone and is therefore very comfortable to wear.

Other objects and features of the present invention will become apparent from the following detailed description considered in connection with the accompanying drawings. It is to be understood, however, that the drawings are designed as an illustration only and not as a definition of the limits of the invention.

In the drawings wherein similar reference characters denote similar elements throughout the several views:

FIG. 1 shows the further processing of a three-member blank formed on a flock wheel into a finished absorbent article, in a diagrammatic sequence in the views a to e;

FIG. 2 is a perspective view of the finished article showing a cross-section taken along line 2—2 of FIG. 1e;

FIG. 3 is a cross-sectional view of the finished article taken along line 3—3 of FIG. 1e.

Figure 4:
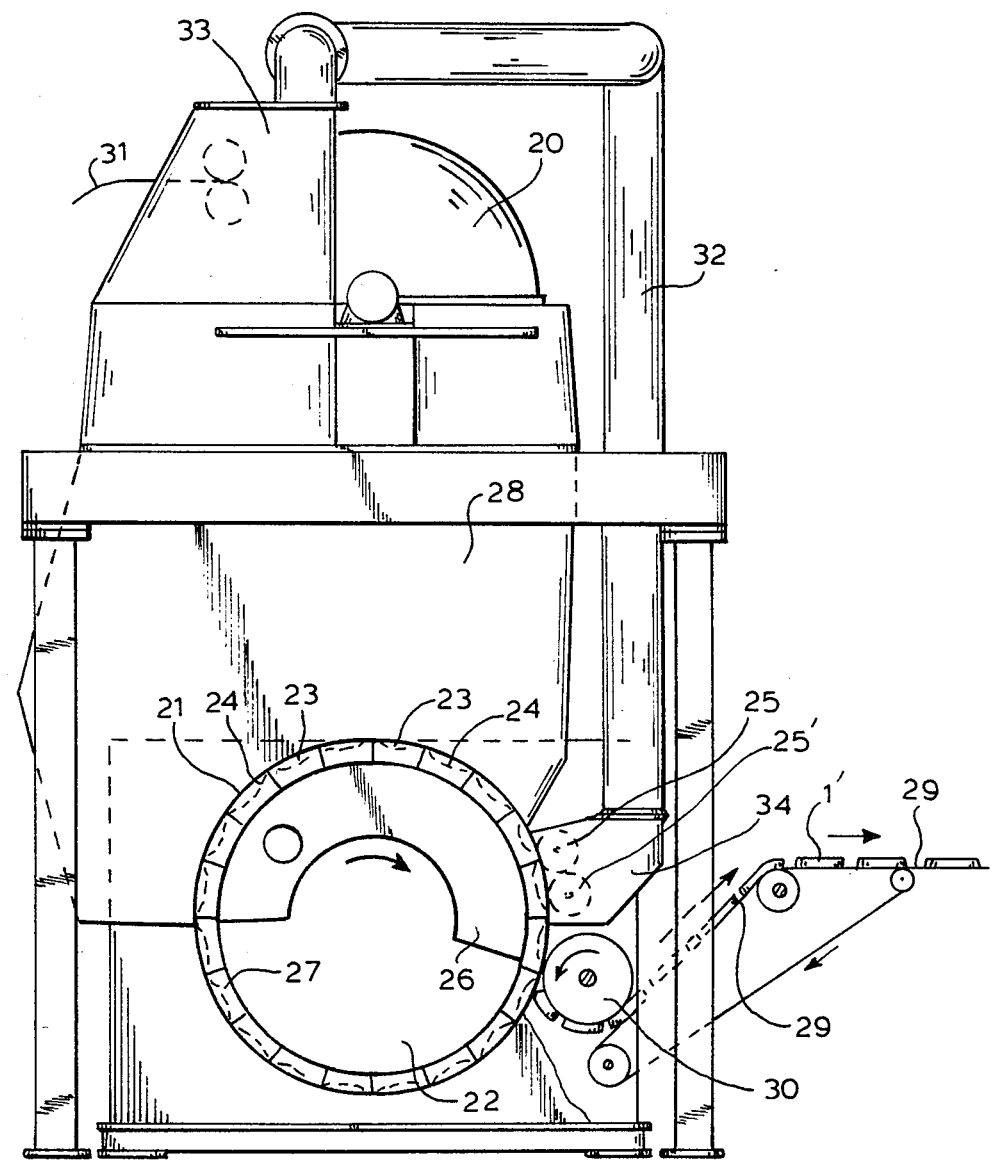
FIG. 4 is a diagrammatic view of the apparatus used in performing the method of the present invention.

Now turning to the drawings, there is shown in FIG. 1, a blank 1' for an absorbent article comprising members 2, 5 and 8. An elongated central member 2 having a rounded front end 3 and a rounded rear end 4 merges by way of its long sides 13 and 14 into symmetrically disposed side members 5 and 8. Members 5 and 8 differ in length from one another and, like member 2, are rounded at their ends 6, 7 and 9, 10.

FIG. 2 shows the finished article 1 as a layered article of generally "e" shaped cross-section; long side member 5 has been folded on central member 2 and short side member 8 has been folded on the back of long side member 5. Because of the generally "e" shaped folding of article 1 natural voids are left between central member 2 and side member 5 and between side member 5 and side member 8 and can receive layers 11 and 12, respectively, of superabsorbent materials.

As can be seen in FIG. 3, after the generally "e" shaped folding of members 2, 5 and 8, a finished absorbent article 1 is provided which is stepped frustum-fashion at its ends 15 and 18. Blank 1' rounded bottom edges 16. As FIG. 3 shows, subsequent to the "e" shaped folding, roundings 16 are at the top in the case of members 5 and 8 but are still at the bottom in the case of member 2.

A description will now be given of the method according to the invention for the preparation of article 1. As can be seen in FIG. 4, cellulose flocks are obtained from an endless cellulose web 31 in a flock mill 33 and are supplied, by means of an air flow produced by a blower 20, through a large tube 28 to a generated cylindrical surface 21 of a rotating flock wheel 27. A suction box 26 is disposed inside wheel 27, the same being in the form of a hollow cylinder. Surface 21 is formed with three-part or three-member shaping recesses 23 whose bases 24 are mesh-like and in air-conveying relationship with interior 22 of the cylinder. The cellulose flakes are sucked from the flow or stream of flocks into recesses 23, the finer flakes first engaging with mesh-like bases 24. The vacuum operative in recesses 23 by way of box 26 and bases 24 compacts and felts the intaken flakes so that three-member blanks 1' which will subsequently become absorbent articles result.

After the stage in which recesses 23 are filled with flock material there follows a combing device 34 which by means of rotating hackles 25, 25' removes the flock material projecting from recesses 23 above surface 21 and returns the material thus removed through a line 32 to blower 20 for reuse. The finished three-member blanks 1' are then removed by a suction roller 30 from recesses 23 and delivered to a conveyor 29 on which they are transported for further processing.

FIG. 1 is a series of diagrammatic views a to e of how blank 1' is given further processing until it becomes a finished absorbent article 1. View a shows the three-member blank 1' as delivered to conveyor 29. Blank 1' comprises an elongated central member 2 which merges by way of its long sides 13 and 14 into symmetrically disposed side members 5 and 8. During conveyance a layer 11 of a superabsorbent material is applied to central member 2, whereafter the long side member 5 is folded onto the surface of member 2, whereafter a layer 12 of a superabsorbent material is applied to the back side of folded-over side member 5. Short side member 8 is then so folded on the back of already folded member 5 that an absorbent article 1 which has an "e" shaped cross-section and ends 15 and 18 stepped like a frustum results.

While only a single embodiment of the present invention has been shown and described, it will be obvious that many changes and modifications may be made thereunto without departing from the spirit and scope of the invention.

What is claimed is:

1. An absorbent article for hygienic purposes, such as sanitary napkins, disposable diapers or the like, comprising a highly absorbent body-fitting one-piece uncut flock member integrally-formed and shaped by a flock wheel and thereby having completely soft edge zones, said flock member having an elongated central member having rounded front and rear ends, said central member merging by way of its long sides into a long side member and a short side member which are symmetrically disposed with respect to said central member and both are provided with rounded front and rear ends, said long side member being folded onto the surface of said central member and said short side member being folded onto the back side of said folded long side member to form a folded absorbent article of generally "3" shaped cross-section which is stepped frustum-fashion at its front end and at its rear end; and a layer of superabsorbent material disposed between at least one pair of the contiguous surfaces of the folded-together members of the article.

2. A method for the manufacture of an absorbent article for hygienic purposes, such as sanitary napkins, disposable diapers or the like, having a highly absorbent body-fitting multipiece flock member, comprising the steps of:

(a) delivering a flow of flock mainly comprising reduced cellulose from a flock mill by a stream of air onto the cylindrical surface of a rotating flock wheel, (b) drawing along a predetermined vacuum path flocks from the flock flow into three-part shaping recesses dispopsed consecutively, in the direction of rotation, on the flock wheel surface, the soft fine flocks first engaging the mesh-like bases of the recesses, (c) compacting and felting the flocks in the recesses to form article blanks in which an elongated central member having rounded front and rear ends merges by way of its long sides into two symmetrically disposed side members differing in length from one another and having rounded front and rear ends, (d) removing the excess flock material projecting beyond the periphery of the surface of the flock wheel and returning the same by a fan to the flock flow, (e) removing the three-member blanks at the end of the vacuum path of the flock wheel by a suction roller from the recesses in the flock wheel and delivering the same to a conveyor, (f) applying portions of superabsorbent materials in predetermined parts to the elongated central member of the blank on the conveyor, and (g) folding the blanks individually and consecutively as considered in the direction of conveyance so that first the long side member is folded onto the surface of the central member, thereafter the short side member is folded onto the back side of the long side member, so that superabsorbent materials are applied between the two folding steps to the back side of the long side member.

3. The method according to claim 2, wherein said shaping recesses in the flock wheel are such that all the edges on the back of the unfolded article are rounded.

* * * * *